US00PP11691P

United States Patent [19]

Zary

[11] Patent Number: Plant 11,691

[45] Date of Patent: Dec. 12, 2000

[54] HYBRID TEA ROSE PLANT NAMED 'JACNEPAL'

[75] Inventor: Keith W. Zary, Thousand Oaks, Calif.

[73] Assignee: Bear Creek Gardens, Inc., Medford, Oreg.

[21] Appl. No.: 09/255,437

[22] Filed: Feb. 22, 1999

[51] Int. Cl.[7] ..... A01H 5/00

[52] U.S. Cl. ..... Plt./132

[58] Field of Search ..... Plt./132, 130

*Primary Examiner*—Howard J. Locker

*Attorney, Agent, or Firm*—Klarquist Sparkman Campbell Leigh & Whinston, LLP

[57] ABSTRACT

A hybrid tea rose plant having vigorous, upright growth; large flowers produced one per stem; mildew and rust resistant foliage; a blend of colors in the flower; and stems long enough for cutting.

1 Drawing Sheet

The present invention relates to a new and distinct variety of rose plant of the hybrid tea class which was originated by me by crossing JACyap (not patented), with MACnewye (U.S. Plant Pat. No. 5,428).

The primary objective of this breeding was to produce a new rose variety having vigorous, upright growth; large flowers produced one per stem; disease resistant foliage; a blend of colors in the flower; and stems long enough for cutting. The objective was substantially achieved, along with other desirable improvements, as evidenced by the following unique combination of characteristics that are otustanding in the new variety and that distinguish it from its parents, as well as from all other varieties of which I am aware:

1. High centered large flowers;
2. Long stems;
3. Blooms one flower per stem;
4. Dark green, glossy, disease resistant foliage;
5. Vigorous, upright growing plant;
6. Flowers that exhibit a blend of colors.

JACnepal is a vigorous, upright, well-branched garden hybrid tea. It produces long-stemmed, large-flowered roses that are a bend of colors. Foliage is dark green, glossy, and very disease resistant.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicted.

Parentage:

*Seed parent.*—JACyap (not patented).

*Pollen parent.*—MACnewye (U.S. Plant Pat. No. 5,428).

Classification:

*Botanical.*—*Rosa hybrida.*

*Commercial.*—Hybrid tea.

FLOWER

Observations made from specimens grown in a garden environment at Somis, Calif. January 1996–December 1998.

Blooming habit: Continuous.

Bud:

*Size.*—1¾ inches long when the petals start to unfurl.

*Form.*—The bud form is long, pointed ovoid.

*Color.*—When sepals first divide, the bud color is Orange-White Group 159D with petal edges and tips Red Group 45D. When half blown, the upper sides of the petals are Orange-White Group 159D with petal edges Red Group 45D, and the lower sides of the petals are Orange-White Group 159D with petal edges Red Group 45D.

*Sepals.*—Color: Green Group 138B except when exposed to direct sunlight. Then, sepals are blushed with Greyed-Purple Group 183D. Surface texture: Covered in fine hairs. There are three normally appendaged sepals. There are two unappendaged sepals with hair edges.

*Receptacle.*—Color: Green Group 137D except when exposed to bright sunlight. Then the color is Greyed-Purple Group 183C. Shape: Funnel. Size: Large (7/16" long×5/8" wide). Surface: Smooth.

*Peduncle.*—Length: Short (averaging 2½ to 3"). Surface: Glandular. Color: Green Group 137D except when exposed to bright sunlight. Then the color is Greyed-Purple Group 183C. Strength: Stiff; erect.

Bloom:

*Size.*—Large. Average open size is 5 to 5½".

*Borne.*—Singly.

*Stems.*—Strength: Strong. Average length is 16–20".

*Form.*—When first open: High centered. Permanence: Retains its form to the end. Outer petals curl back.

*Petalage.*—Number of petals under normal conditions: 30–35.

*Color.*—The upper sides of the petals are Orange-White Group 159D with petal edges Red Group 45D. The reverse sides of the petals are Orange-White Group 159D with petal edges Red Group 45D. The base of each petal has on both surfaces a ¼×¼" Yellow Group 12B half moon at the point of attachment. The major color on the upper sides is Orange-White Group 159D.

*Variegations.*—None.

*Discoloration.*—At the end of the first day: No change. At the end of the third day: No change. By day five or six, on the plant, there is a fading of color on the petal edges to Red Group 48B.

*Fragrance.*—Moderate; spicy.

Petals:

*Texture.*—Thick.

*Shape.*—Round.

*Form.*—Tips slightly recurved.

*Arrangement.*—Imbricated. Petaloids in the center: None.

*Persistence.*—Petals drop off cleanly before drying.

*Lastingness.*—On the plant: Long (7 days). As a cut flower: Long (8–9 days).

Reproductive parts:

*Anthers.*—Size: Medium. Quantity: Many. Color: Yellow-Orange Group 17D. Arrangement: Regular around styles.

*Filaments.*—Color: Red Group 45C.

*Pollen.*—Color: Yellow-Orange Group 22A.

*Styles.*—Color: Red Group 53B.

*Stigmas.*—Color: Yellow-White Group 158C.

Plant:

*Form.*—Bush.

*Growth.*—Vigorous; upright; branching.

*Mature plant.*—Height 5½ to 6', and width is 3½'.

Foliage: Number of leaflets on normal mid-stem leaves: 5 or 7.

*Size.*—Large (6 to 6½" long×5 to 5½" wide.).

*Quantity.*—Abundant.

*Color.*—New foliage: Upper Surface: Greyed-Orange 176A. Lower Surface: Greyed-Orange 176C. Old foliage: Upper Surface: Green Group 139A. Lower Surface: Green Group 138A.

*Shape.*—Pointed oval.

*Texture.*—Upper side: Leathery; glossy.

*Edge.*—Serrated.

*Serration.*—Single; small.

*Petiole rachis.*—Color: Upper surface: Greyed-Purple Group 183A. Lower Surface: Green Group 137D.

*Petiole underside.*—Rough; with prickles.

*Stipules.*—Medium (⅝"); serrated; bearded.

*Disease resistance.*—Susceptible to blackspot, and resistant to rust and mildew under normal growing conditions.

Wood:

*New wood.*—Color: Greyed-Orange Group 176A. Bark: Smooth.

*Old wood.*—Color: Green Group 137B. Bark: Smooth.

Prickles:

*Quantity.*—On main canes from base: Ordinary. On laterals from main canes: Ordinary.

*Form.*—Medium; hooked downward.

*Color when young.*—Greyed-Purple Group 187B.

*Color when mature.*—Greyed-Orange 173C.

Small prickles:

*Quantity.*—On main stalks: None. On laterals: None.

I claim:

1. A new and distinct variety of rose plant of the hybrid tea class, substantially as herein shown and described, characterized particularly as to novelty by its vigorous, upright growth; large flowers produced one per stem; mildew and rust resistant foliage; a blend of colors in the flower; and stems long enough for cutting.

* * * * *

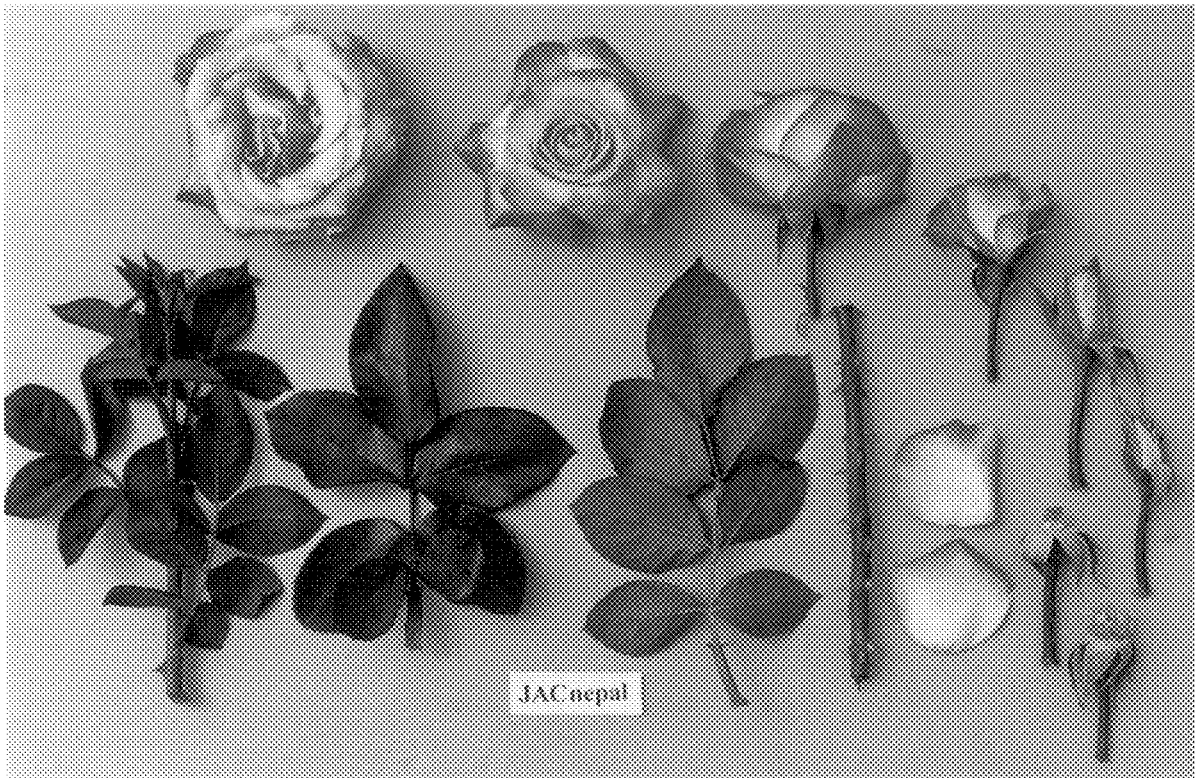
JACnepal